(12) United States Patent
Larsson

(10) Patent No.: US 8,317,768 B2
(45) Date of Patent: Nov. 27, 2012

(54) ABSORBENT ARTICLE

(75) Inventor: Gunnar Larsson, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 449 days.

(21) Appl. No.: 12/666,899

(22) PCT Filed: Jul. 5, 2007

(86) PCT No.: PCT/SE2007/050499
§ 371 (c)(1),
(2), (4) Date: Dec. 28, 2009

(87) PCT Pub. No.: WO2009/005431
PCT Pub. Date: Jan. 8, 2009

(65) Prior Publication Data
US 2010/0331804 A1 Dec. 30, 2010

(51) Int. Cl.
*A61F 13/15* (2006.01)
*A61F 13/20* (2006.01)
(52) U.S. Cl. ............... 604/385.24; 604/385.23
(58) Field of Classification Search ............. 604/385.23, 604/385.24
See application file for complete search history.

(56) References Cited

U.S. PATENT DOCUMENTS

| | | | |
|---|---|---|---|
| 4,624,666 A | 11/1986 | DeRossett et al. | |
| 4,695,278 A | 9/1987 | Lawson | |
| 5,188,624 A * | 2/1993 | Young et al. | 604/378 |
| 5,300,053 A | 4/1994 | Genaro | |
| 6,293,933 B1 | 9/2001 | Ahlstrand | |
| 7,686,790 B2 * | 3/2010 | Rasmussen et al. | 604/317 |
| 2004/0143233 A1 | 7/2004 | Nakajima et al. | |
| 2004/0243078 A1 * | 12/2004 | Guidotti et al. | 604/367 |
| 2005/0148258 A1 | 7/2005 | Chakravarty et al. | |
| 2007/0073254 A1 * | 3/2007 | Ponomarenko et al. | 604/383 |
| 2009/0112175 A1 * | 4/2009 | Bissah et al. | 604/385.101 |
| 2010/0280474 A1 * | 11/2010 | Bruzadin et al. | 604/378 |

FOREIGN PATENT DOCUMENTS

| | | |
|---|---|---|
| EP | 1 421 926 A1 | 5/2004 |
| GB | 2 319 730 A | 6/1998 |
| WO | WO 96/12457 A1 | 5/1996 |
| WO | WO 97/17922 A1 | 5/1997 |
| WO | WO 2005/065611 A1 | 7/2005 |

OTHER PUBLICATIONS

International Search Report of Application No. PCT/SE2007/050499 dated Mar. 26, 2008.

* cited by examiner

*Primary Examiner* — Susan Su
(74) *Attorney, Agent, or Firm* — Buchanan Ingersoll & Rooney PC

(57) ABSTRACT

An absorbent article (1), such as an incontinence protector, sanitary napkin or the like, includes a liquid permeable top sheet (3), a backing sheet (4) and an absorbent core (5,6,7) enclosed therebetween. The absorbent core includes an upper absorbent layer (5) proximal to the top sheet and a lower absorbent layer (6) distal to the top sheet. An elongated hole (8) extending in the longitudinal direction of the article is made in the absorbent core. First and second elastic elements (9,10) attached to opposite lateral edges of the absorbent core (5,6,7) extend along the hole in a longitudinal direction and the top sheet (3) is affixed to the elastic elements and to the bottom of the hole (8).

13 Claims, 2 Drawing Sheets

ABSORBENT ARTICLE

TECHNICAL FIELD

The invention relates to an absorbent article, such as an incontinence protector, sanitary napkin or the like, having a liquid permeable top sheet, a backing sheet and an absorbent core enclosed therebetween, said absorbent core including an upper absorbent layer proximal to the top sheet and a lower absorbent layer distal to the top sheet, wherein an elongated hole extending in the longitudinal direction of the article is made in the absorbent core.

BACKGROUND TO THE INVENTION

In order to enable incontinence protectors to receive large amounts of momentarily emitted urine is it advantageous that the protector has a bowl shape. Such a bowl functions as a temporary storage space during the time it takes for the emitted urine to be sucked into the absorbent core of the protector. Many incontinence protectors are for this reason provided with elastic elements in order to give the protector its desired bowl shape, see for example WO 97/17922 A1. Another way of providing a temporary storage space and at the same time enhance the ability of a protector to store absorbed liquid in a portion thereof distal from the body of the wearer is to provide a hole in the absorbent layer closest to the body of the wearer, see for example WO 2005/065611 A1 and U.S. Pat. No. 5,300,053.

Incontinence protectors and the like absorbent articles are usually packaged in a folded and planar state. Such products do normally not have the desired bowl shape when taken out of the package and consequently the user has to shape the article to the desired bowl shape before it is applied. After such shaping of the article, the elastic elements will maintain the bowl shape during use of the article.

It is an objective of the present invention to create an absorbent article of the above mentioned kind which by itself creates a desired bowl shape when taken out of its package. It is also an objective of the invention to create such an article in which the absorbent core is close to the user's body when the article is applied.

SUMMARY OF THE INVENTION

These objectives are accomplished by an absorbent article, such as an incontinence protector, sanitary napkin or the like, having a liquid permeable top sheet, a backing sheet and an absorbent core enclosed therebetween, said absorbent core including an upper absorbent layer proximal to the top sheet and a lower absorbent layer distal to the top sheet, wherein an elongated hole extending in the longitudinal direction of the article is made in the absorbent core, characterised in that first and second elastic elements attached to opposite lateral edges of the absorbent core extend along said hole in a longitudinal direction and said top sheet is affixed to said elastic elements and to the bottom of said hole.

In such an article, said elongated hole does not only serve as a storage space for emitted liquid but also as guide lines for controlling which portions of the absorbent core that will be raised due to the pretension in the elastic elements. The attachment of the elastic elements to the absorbent core instead of outside the core has the consequence that the absorbent core will be placed nearer the body of the user during use of the article. The attachment of the top sheet to the elastic elements and to the bottom of the hole will hold the major part of the top sheet away from the body of a wearer. Thereby the risk to have a wet surface in abutment to the body of a user is reduced.

In a preferred embodiment said elastic elements are extended beyond said hole in the longitudinal direction, at least beyond the front portion of said hole, and said hole has the form of an Y, the central leg of said Y being extended along the longitudinal axis of the article and the legs of said Y diverging from said central leg being closer to the front end of the article than the central leg. The Y-shape of the hole makes the front portion of the article containing the diverging legs wider than portion of the article containing the central leg. This gives the article a good fit on a user preventing rearward sliding of an applied article.

Said hole goes preferably trough said upper absorbent layer of the absorbent core and an acquisition layer is disposed between the upper and lower absorbent layers of the absorbent core. Said acquisition layer extends beyond the longitudinal and lateral extension of said hole in the upper absorbent layer of the absorbent core.

The lower absorbent layer has preferably a larger extension than the acquisition layer both in the longitudinal and the lateral direction and the upper absorbent layer extend beyond the lower absorbent layer in the longitudinal direction.

To advantage a third elastic element extends along the longitudinal axis of the article from the rear end of said hole to the rear end of the article or the absorbent core and is attached to the upper absorbent layer and to the top sheet. Such a third elastic element gives the rear portion of the article a better fit.

Each elastic element consists preferably of a band of an elastic foam material or an elastic nonwoven and the elastic elements are preferably liquid permeable.

The pretension in the first and second elastic element shall be such that the portion of the article being forward of the point in which the three legs of the Y-shaped hole in the upper absorbent layer meet, forms an angle greater than 30 degrees to the horizontal when the portion of the article located rearward of said point is held in a horizontal position. In addition to being a prerequisite for obtaining a desired bowl shape this feature indicates in a simple way to the user where the article should be applied on the body of the user and facilitates thus an application of the article.

The upper absorbent layer consists in the preferred embodiment of a mixture of pulp and SAP and the lower absorbent layer consists of pulp with approximately 30% SAP mixed therein. The acquisition layer consists of a nonwoven through air wadding.

Optionally can a stiffening element be disposed proximal to the backing sheet, if the stiffness of absorbent core is to low.

BRIEF DESCRIPTION OF THE DRAWINGS

The invention will now be described with reference to the enclosed Figures, of which.

DESCRIPTION OF EMBODIMENTS

Figure 2:
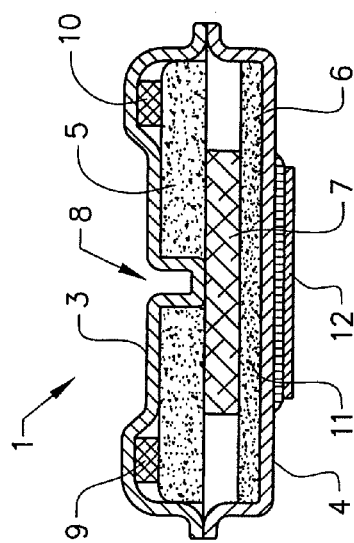
FIG. 2 is a sectional view along line II-II in FIG. 1, FIG. 3 schematically shows a perspective view of the absorbent article in FIG. 1 with the elastic elements in a contracted state.
Figure 1:
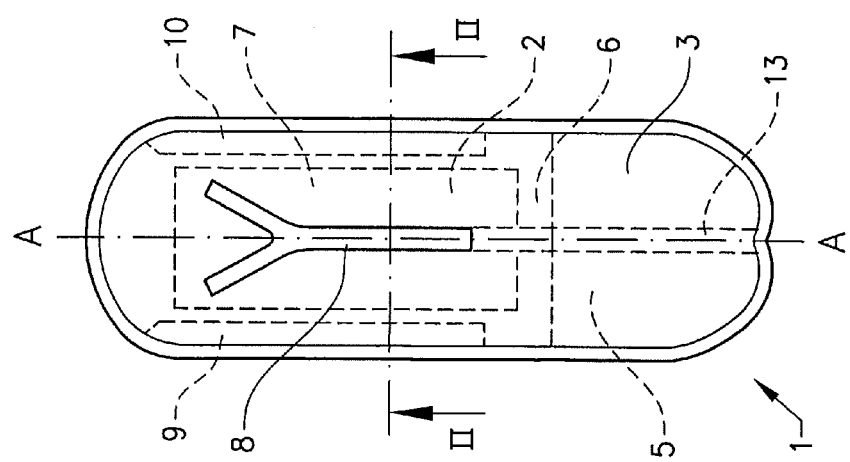
FIG. 1 schematically shows a plan view of an absorbent article according to a preferred embodiment, the article shown in planar state, i.e. all elastic elements are stretched.

FIGS. 1 and 2 disclose an absorbent article 1 in form of a protector for light incontinent females in a planar state, i.e. the state such articles are held in during manufacturing thereof. The article 1 is composed of an absorbent body or core 2 enclosed between a top sheet 3 and a backing sheet 4. The top sheet 3 and backing sheet 4 extend beyond the absorbent core 2 around its whole circumference and are attached to each other in the portions extending beyond the core.

The absorbent core 2 consists of three layers; an upper absorbent layer 5 being proximal to the top sheet, a lower absorbent layer 6 being distal to the top sheet and an acquisition layer 7 disposed between the upper and lower absorbent layers. A through-going hole 8 having Y-shape is made in the upper absorbent layer 5. The central leg of said Y is extended along the longitudinal axis of the article and the legs of said Y diverging from said central leg are closer to the front end of the article, i.e. the upper end in FIG. 1, than the central leg. The major part of hole 8 is disposed in the front half of the article 1.

Two elastic bands 9 and 10 are attached in a pre-tensioned state to opposite longitudinal edges of upper absorbent layer and extend along said hole 8 parallel to the longitudinal axis A-A. These elastic bands extend beyond the hole 8 in the longitudinal direction, at least in the front portion of the article. The top sheet 3 is attached to these elastic bands 9,10 and also to the bottom of hole 8, i.e. to the upper side of the acquisition layer 7.

The article 1 also comprises a layer of adhesive 11 for releasably attaching the article to the inside of a pair of underpants and a release layer 12 protecting the adhesive layer before use.

The article 1 also comprises a third elastic band 13 extending along the longitudinal axis A-A from the rear end portion of hole 8 to the rear end of the article.

The acquisition layer 7 extends beyond the hole 8 both in a longitudinal direction and in a lateral direction. The lower absorbent layer 6 has a greater extension than the acquisition layer both in a longitudinal and lateral direction but is shorter than the upper absorbent layer 5 in the longitudinal direction so that the upper absorbent layer 5 is the only layer of the absorbent core in a rear end portion of the absorbent core.

Figure 3:
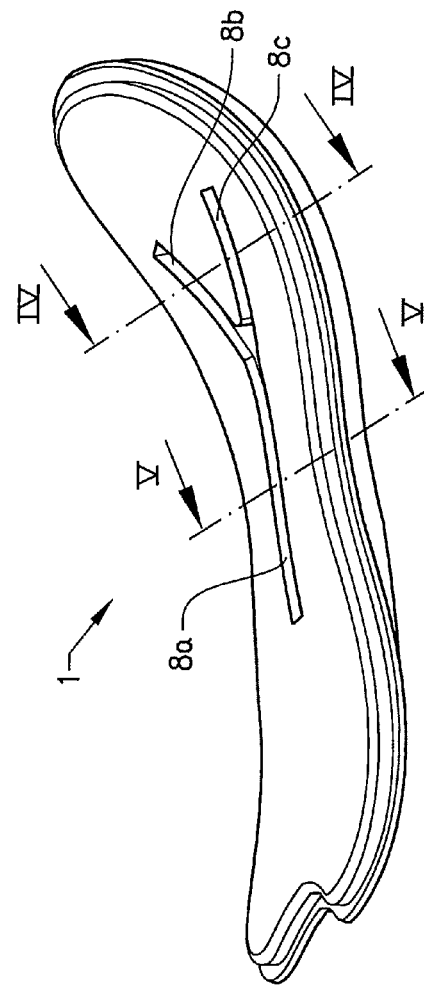
Figure 4:
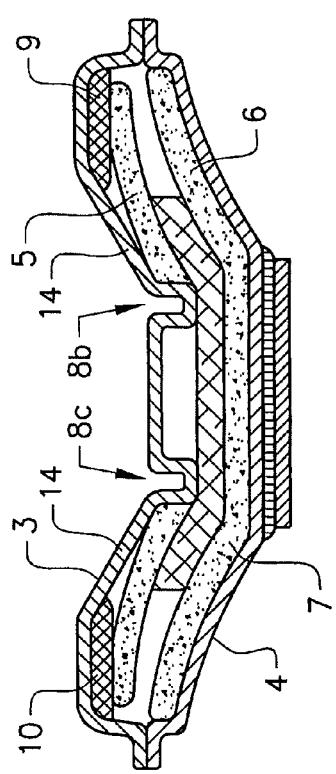
FIG. 4 is a sectional view along line IV-IV in FIG. 3.
Figure 5:
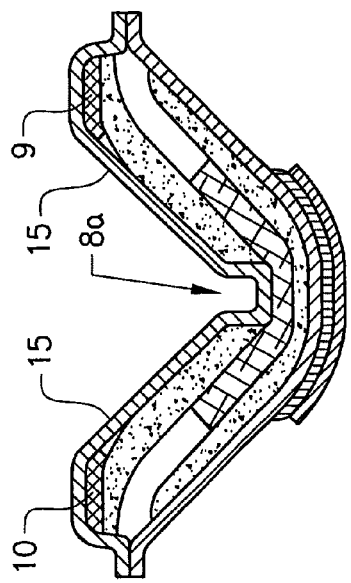
FIG. 5 is a sectional view along line V-V in FIG. 3.

FIG. 3 is a schematic perspective view of the article 1 after that the pre-tensioned elastic bands 9, 10 and 13 have been allowed to contract after manufacture of the article. As is evident from FIG. 3, the forward part of the article has been raised above the remaining part thereof due to the contraction, i.e. the shortening, of the elastic bands 9 and 10. Moreover, the portions of the absorbent core disposed laterally of the hole 8 have been folded up, the channels 8a,8b and 8c in the upper absorbent layer formed by hole 8 functioning as folding lines. Thereby, a bowl shape is formed both in the front portion of the article containing channels 8b and 8c and the middle portion containing channel 8a. In the front portion, a triangular unfolded part (see FIG. 4) is present in the region between the diverging legs 8b and 8c of the Y-shaped hole 8 and forms the bottom of bowl. The parts of the front portion of the absorbent core disposed laterally of legs or channels 8b and 8c constitute walls 14 of the bowl in the front portion. These parts have a triangular configuration with their apices directed forward, i.e. in the opposite direction as the apex of the bottom of the bowl. In the middle portion (see FIG. 5), the bowl shaped has the form of a valley. The walls 15 in the valley-shaped bowl in the middle portion of the article have a larger height than the walls 14 in the front part of the front portion of the article and consequently the article is wider in this front portion than in the middle portion. Behind the rear end of the channel 8a in the middle portion the height of the walls 15 will rapidly decrease so that the rear portion of the article will essentially be planar. In the middle portion of the article containing the channel 8a, the article will thus be narrower than in both the front and rear portion thereof as is schematically indicated in FIG. 3.

In the rear end portion of the article 1, the contraction of the elastic band 13 gives the end part a slightly upwardly curved configuration.

Figure 6:
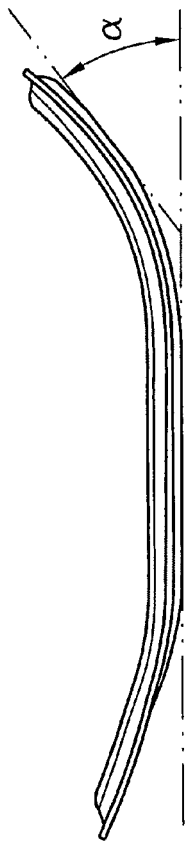
FIG. 6 is a schematic side view of the article in FIG. 3.

In FIG. 6 a side view of the article 1 according to FIG. 3 is shown. As is evident from this Figure most of the curving in the longitudinal direction of the absorbent core due to the contraction of elastic bands 9,10 occur in a region located longitudinally around the point where the three legs of hole 8 meet. The region containing the bottom of the bowl formed in the front portion will remain substantially planar as well as the region containing the central leg 8a of the hole 8. When the latter region is placed on a horizontal plane, as in FIG. 6, an angle α can be defined between the above mentioned two regions along the longitudinal symmetry lines thereof. The value of this angle will be dependent on the contractive forces of the pre-tensioned elastic bands 9, 10. In the sense of the present invention, the contractive forces shall be so strong that the angle α is greater than 30 degrees.

Incontinence protectors, sanitary napkins and the like articles are usually packaged in a folded and planar state. In known articles of this kind with elastic elements provided outside of the absorbent core, the user must usually manually create the bowl form of the article which then is maintained by the elastics. When article 1 is taken out of a package it assumes by itself the configuration schematically disclosed in FIGS. 3-6 and the article is thus ready for application directly after being taken out of its package. Furthermore, the configuration of article 1 is very well adapted to the female body and the curvature of the article also indicates clearly to the user where the article should be located in relation to the body. The greater width of the article in the front portion contributes to hold an applied article in place so that it does not slide rearwards due to movements of the user.

The placement and attachment of the elastic bands onto the absorbent core will hold the core closer to the body of the user compared with similar articles having elastic elements located outside the absorbent core. Moreover, the attachment of the top sheet 3 to the bottom of hole 8 prevents the top sheet from leaving the surface of the absorbent core during folding up of the walls of the bowls. The top sheet material in the centre, the wetting area, will thus be held away from the body of the user in the bowl formed in the front and middle portions so that the risk for having a wet surface abutting the body of the user is reduced.

In the applied state of article 1, the elastic band 13 will contribute to hold the rear portion of the article against the body of the user between the buttocks of the user. In the portion of the article which in use is to be disposed between the buttocks of the user, the absorbent core only contains the upper absorbent layer. The absorbent core can therefore easily deform to follow the shape of the buttocks.

The liquid-permeable top sheet 3 can be made any material used as top sheet material for absorbent articles, such as sanitary napkins, diapers and incontinence protectors. It can for example be a nonwoven material, a perforated plastic film or a laminate of two or more layers. Preferably, the top sheet is made of hydrophobic material. In the embodiment described above, the top sheet is attached to the elastic bands 9,10 as well as the bottom of the hole but it is of course possible to attach the top sheet also to the upper absorbent layer. Such an attachment must be liquid permeable and can be made using liquid-permeable adhesive or a pattern of adhesive spots or strings.

The elastic band 9,10 and 13 can be made of different kinds of elastic material, for example an elastic foam, but can also consist of a strip of elastic material, such as elastic nonwoven, elastic plastic film or several threads of elastic material laminated to one or two layers of non-elastic material, such as nonwovens. A suitable elastic band is an elastic foam from CALLIGEN FOAM Ltd, England, sold under the trade name ELASTIC FOAM XD4100 AS. In order to distribute the elastic force of the pre-tensioned bands 9,10 on a relatively large area of the upper absorbent layer while leaving the created bowls substantially uncovered, the width of each band should be 10-20% of the width of the article.

By elastic material is in the present application meant a material that recovers at least 10% after elongation, preferably at least 25%.

The upper absorbent layer 5 can consist of any known absorbent material used for absorbent articles, such as sanitary napkins, diapers and incontinence protectors. It can consist of cellulose fluff preferably mixed with super absorbent particles (SAP). One example of a suitable material for the upper absorbent layer is pulp mixed with approximately 30% of SAP from BASF, Ludwigshafen, Germany available under the trade name B7160. The mixture of cellulose fluff and SAP has preferably a density of 0.083-0.125 g/cm$^3$.

The acquisition material 7 can consist of any material used as acquisition material for absorbent articles, such as sanitary napkins, diapers and incontinence protectors. It is an open material, which easily will pass received liquid to the underlying lower absorbent layer. Furthermore, it shall not collapse after receiving liquid but remain open. A suitable material for the acquisition layer is a hydrophobic wadding of through air nonwoven available from LIBELTEX, Belgium having the trade name DRY WEB T 23W.

The lower absorbent layer 6 can consist of a material similar to the material in the upper absorbent layer. However, the capillaries in the lower absorbent layer should be smaller than in the upper absorbent layer so that liquid temporarily stored in the acquisition layer will first be sucked up by the lower absorbent layer. Thereby most of the liquid emitted by a user of the article will be stored in the lower absorbent layer and only a small amount of liquid will be absorbed and stored in the upper absorbent layer. A suitable material for the lower absorbent layer is pulp with approximately 35% of SAP of the same or a similar quality as for the upper absorbent layer.

Furthermore, SAP in the lower layer 6 have the main function of increasing the liquid storing capacity of this layer whereas the main function of possible SAP in the upper layer 5 is to prevent rewet of liquid absorbed in this layer if the article is compressed by external forces during use, for example when the user is cycling. The SAP in the upper absorbent layer will thus advantageously be of a different type than SAP used in the lower absorbent layer or be present in a lower percentage than in the lower absorbent layer.

The backing sheet can be made of any material used as backing sheet in absorbent articles, such as sanitary napkins, diapers and incontinence protectors. It can for example consist of a plastic film, a liquid-impermeable nonwoven material comprising one or more layers and/or a laminate of a plastic film and a nonwoven material.

As stated above, the contractive forces of the pre-tensioned elastic bands 9,10 should be so strong that the angle α (see FIG. 6) will be greater than 30 degrees. The forces needed are thus dependent on the size of the article and the materials and thicknesses of the different layers in the absorbent core and can therefore not be easily defined. However, the angle α is well suited to define the pre-tensioned needed.

Furthermore, the absorbent core should have such a stiffness and strength that shape of the article described with reference to FIGS. 3-6 is obtained without local rupture or local disintegration in any of the layers making up the absorbent core. The upper and lower absorbent layers usually have the required strength and stiffness and do not create any problem in this respect. If there is a risk that local rupture or disintegration should occur, the integrity of the different layers can be ensured by inserting a stiffening element between the lower absorbent layer and the backing sheet. Such a stiffening element can consist of a plastic sheet with or without folding lines, a hydrophobic nonwoven material, a paper material with a hydrophobic surface, etc.

The Y-shape of the hole 8 can be varied in order to create the desired bowl-shape in the front and middle portions of the article by varying the angle between the diverging legs 8b,8c of the Y and by the varying the relative length of the different legs of the Y. Also the width of the legs can be varied. However, the outer angle between leg 8a and the respective legs 8b,8c should always be greater than 90 degrees.

As stated above, the legs of the hole 8 functions as folding lines for the absorbent core. Thereby the middle portion of the article in use being disposed between the thighs of the user can easily follow the movements of the thighs only by varying the angle of folding around the edge of the leg 8a without deformation of the absorbent core. The elastic bands 9,10 will bias the walls of the valley-shaped bowl in the middle portion of the article to the position shown in FIGS. 3-6 when then article is not subjected to external forces.

The article 1 can be manufactured in a conventional way by laying a row of absorbent cores on a continuously running web of casing material, applying a second web of casing material onto the web containing the row of absorbent cores, attaching the webs to each other, thereby creating a row of article blanks connected to each other, and finally cutting individual articles 1 out of the row of article blanks. The elastic bands 9,10 and 13 are preferably attached to the web of top sheet material before it is applied over the row of absorbent cores or before the absorbent cores are laid onto the web, depending on which of the webs, i.e. the web of top sheet material or the web of backing sheet material, the absorbent cores are laid upon. The manufacture is facilitated by all the elastic bands being applied in a straight state. After manufacture, the absorbent articles are packaged. The packaging can include folding first the rear third of the article onto the middle portion and thereafter folding the front third portion over the in-folded rear portion.

The described embodiments can of course be modified in several respects without leaving the scope of invention. For example, the lower absorbent layer can have the same shape as the upper absorbent layer and the acquisition layer can have a greater extension. The elastic band 13 in the rear portion of the article can be deleted. The pre-tension in the band can be varied so that the pre-tension in the rear elastic band 13 is lower or higher than in the bands 9,10. The adhesive layer 11 need not be homogenous but can consist of several strings of adhesive or a pattern of adhesive. It is also possible to substitute this adhesive layer by a frictional material or hooks type material. The elastic bands need not to be liquid-permeable, even if this is preferred, and thus need the adhesive used to attach these bands to the top sheet and the upper absorbent layer not be liquid-permeable, even if this is preferred. If thermoplastic fibres are present in the upper absorbent layer, the attachment of this layer to the elastic bands can be made by welding with the aid of an ultra-sonic welding device or other heat-sealing devices. The shape of the article can also differ. The scope of protection should therefore not be limited by the described embodiments but be defined by the enclosed patent claims.

The invention claimed is:

1. An absorbent article comprising:
a liquid permeable top sheet;
a backing sheet;
an absorbent core enclosed therebetween;
an elongated hole extending in a longitudinal direction of the article is made in the absorbent core; and
first and second elastic elements attached to opposite lateral edges of the absorbent core extending along said hole in the longitudinal direction and said top sheet is affixed to said elastic elements and to a bottom of said hole, wherein said absorbent core includes an upper absorbent layer proximal to the top sheet and a lower absorbent layer distal to the top sheet, and said hole has the form of a Y, the central leg of said Y being extended along a longitudinal axis of the article and the legs of said Y diverging from said central leg being closer to the front end of the article than the central leg,
wherein a third elastic element extends along the longitudinal axis of the article from a rear end of said hole to a rear end of the article or a rear end of the absorbent core and is attached to the upper absorbent layer and to the top sheet.

2. The absorbent article according to claim 1, wherein each elastic element consists of a band of an elastic foam material.

3. The absorbent article according to claim 2, wherein the elastic elements are liquid permeable.

4. The absorbent article according to claim 1, wherein an acquisition layer is disposed between the upper and lower absorbent layers of the absorbent core and wherein the top sheet affixed to the bottom of the hole is affixed to an upper side of the acquisition layer.

5. The absorbent article according to claim 4, wherein said first and second elastic elements are extended beyond said hole in the longitudinal direction, at least beyond the front portion of said hole.

6. The absorbent article according to claim 5, wherein said hole goes through said upper absorbent layer of the absorbent core.

7. The absorbent article according to claim 4, wherein said acquisition layer extends beyond the longitudinal and lateral extensions of said hole in the upper absorbent layer of the absorbent core.

8. The absorbent article according to claim 7, wherein the lower absorbent layer has a larger extension than the acquisition layer both in the longitudinal direction and the lateral direction.

9. The absorbent article according to claim 8, wherein the upper absorbent layer extends beyond the lower absorbent layer in the longitudinal direction.

10. The absorbent article according to claim 4, wherein the tension in the first and second elastic elements is such that the portion of the article being forward of the point in which the three legs of the Y-shaped hole in the upper absorbent layer meet, forms an angle greater than 30 degrees to the horizontal when the portion of the article located rearward of said point is held in a horizontal position.

11. The absorbent article according to claim 4, wherein the upper absorbent layer consists of a mixture of pulp and SAP and the lower absorbent layer consists of a mixture of pulp and SAP, the percentage of SAP in the mixtures being higher in the lower absorbent layer.

12. The absorbent article according to claim 4, wherein the acquisition layer consists of through air nonwoven.

13. The absorbent article according to claim 4, wherein a stiffening element is disposed proximal to the backing sheet.

* * * * *